(12) United States Patent
Takaki et al.

(10) Patent No.: US 6,294,704 B1
(45) Date of Patent: *Sep. 25, 2001

(54) METHOD FOR MANUFACTURING FLUOROALCOHOL

(75) Inventors: Shoji Takaki; Toru Yoshizawa, both of Settsu (JP)

(73) Assignee: Daikin Industries, Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/394,672

(22) Filed: Sep. 13, 1999

(30) Foreign Application Priority Data

Mar. 15, 1999 (JP) .................................................. 11-067714

(51) Int. Cl.⁷ ............................. C07C 29/80; C07C 29/44
(52) U.S. Cl. ........................................... 568/842; 568/904
(58) Field of Search ..................................... 568/842, 904

(56) References Cited

U.S. PATENT DOCUMENTS

| 2,559,628 | 7/1951 | Joyce, Jr. et al. ................... 260/633 |
| 4,346,250 | 8/1982 | Satokawa et al. ................... 568/842 |
| 5,023,377 | * 6/1991 | Desmarteau et al. ............... 564/301 |

FOREIGN PATENT DOCUMENTS

| 0 398 154 A1 | 11/1990 | (EP) . |
| 0 524 638 A2 | 1/1993 | (EP) . |
| 0 967 193 A2 | 12/1999 | (EP) . |
| 4-8585 | 1/1992 | (JP) . |
| 5-225619 | 9/1993 | (JP) . |
| 5-258346 | 10/1993 | (JP) . |

* cited by examiner

*Primary Examiner*—Peter O'Sullivan
(74) *Attorney, Agent, or Firm*—Larson & Taylor, PLC

(57) ABSTRACT

The invention relates to a method for manufacturing a fluoroalcohol represented by formula (1)

$$H(CFR^1CF_2)_nCH_2OH \qquad (1)$$

(wherein $R^1$ represents F or $CF_3$, when n=1; $R^1$ represents F, when n=2) by reacting methanol with tetrafluoroethylene or hexafluoropropylene in the presence of a free radical generator, wherein the method comprises the steps of: feeding a reaction mixture into a distillation column; distilling off methanol from the top of the distillation column; withdrawing a bottom fraction comprising the fluoroalcohol from the bottom of the distillation column; removing a fraction comprising water and HF from the distillation column by side cut; feeding methanol from the top of the distillation column back into a reactor for recycling; and purifying the bottom fraction to recover the fluoroalcohol represented by formula (1).

2 Claims, 1 Drawing Sheet

METHOD FOR MANUFACTURING FLUOROALCOHOL

FIELD OF THE INVENTION

The invention relates to a method for manufacturing a fluoroalcohol represented by formula (1)

$$H(CFR^1CF_2)_nCH_2OH \quad (1)$$

wherein $R^1$ represents F or $CF_3$, when n=1; $R^1$ represents F, when n=2.

BACKGROUND ART

With respect to a method for manufacturing $H(CF_2CF_2)_nCH_2OH$ (n=1,2), Japanese Unexamined Patent Publication 154707/1979 and U.S. Pat. No. 2,559,628 disclose that a telomer mixture comprising $H(CF_2CF_2)_nCH_2OH$ (n=1 to 12) is prepared by reacting excess methanol with tetrafluoroethylene in the presence of t-butyloctylperoxide.

Methanol should be recovered efficiently in the reaction, since excess methanol is used.

It is an object of the invention to provide a method for manufacturing fluoroalcohol in which methanol is recovered efficiently.

DISCLOSURE OF THE INVENTION

Figure 1:
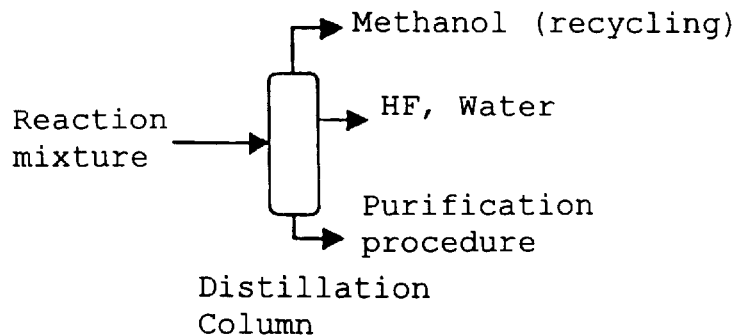
FIG. 1 shows one embodiment of the invention.

The inventors conducted extensive research on recovery of methanol from a reaction mixture and found that water and HF contamination of recovered methanol inhibited a reaction when the recovered methanol was recycled to a reactor and that efficient recovery of methanol was able to be carried out by recovering water and HF separated from methanol.

The invention relates to the following 1 and 2.

1. A method for manufacturing a fluoroalcohol represented by formula (1)

$$H(CFR^1CF_2)_nCH_2OH \quad (1)$$

(wherein $R^1$ represents F or $CF_3$, when n=1; $R^1$ represents F, when n=2) by reacting methanol with tetrafluoroethylene or hexafluoropropylene in the presence of a free radical generator, wherein the method comprises the steps of:

feeding a reaction mixture into a distillation column;
distilling off methanol from the top of the distillation column,
withdrawing a bottom fraction comprising the fluoroalcohols from the bottom of the distillation column;
removing a fraction comprising water and HF from the distillation column by side cut;
feeding methanol from the top of the distillation column back into a reactor for recycling; and
purifying the bottom fraction to recover the fluoroalcohol represented by formula (1) (hereinafter referred to as "first invention").

2. A method for manufacturing a fluoroalcohol represented by formula (1)

$$H(CFR^1CF_2)_nCH_2OH \quad (1)$$

(wherein $R^1$ represents F or $CF_3$, when n=1; $R^1$ represents F, when n=2) by reacting methanol with tetrafluoroethylene or hexafluoropropylene in the presence of a free radical generator, wherein the method comprises the steps of:

feeding a reaction mixture into a first distillation column;
distilling off methanol from the top of the first distillation column;
withdrawing a first bottom fraction comprising water, HF and the fluoroalcohol represented by formula (1) from the bottom of the first distillation column;
feeding the first bottom fraction into a second distillation column;
withdrawing a fraction comprising water and HF from the top of the second distillation column;
withdrawing a second bottom fraction comprising the fluoroalcohol represented by formula (1) from the bottom of the second distillation column;
feeding methanol from the top of the first distillation column back into a reactor for recycling; and purifying the second bottom fraction to recover the fluoroalcohol represented by formula (1) (hereinafter referred to as "second invention").

In carrying out the method of the invention, excess methanol is used based on tetrafluoroethylene or hexafluoropropylene. Reaction temperature ranges from about 40 to about 140° C. Reaction time ranges from about 3 to about 12 hours. Reaction pressure ranges from about 0.2 to about 1.2 MPa. The reaction may be conducted in an autoclave. The air in the reactor is preferably replaced by nitrogen, argon and like inert gas.

The reaction to manufacture the fluoroalcohol is preferably conducted in the presence of an acid-acceptor. Examples of acid-acceptor are calcium carbonate, magnesium carbonate, sodium carbonate, potassium carbonate, sodium bicarbonate, potassium bicarbonate, barium carbonate and like alkali metal carbonates and bicarbonates and alkaline earth metal carbonates, calcium oxide, calcium hydroxide and soda lime. The acid-acceptor preferably traps acid such as HF generated during the reaction without strongly basifying the reaction mixture.

The amount of the acid-acceptor used in the reaction is not specifically limited to, but ranges from 0.001 to 0.1 mole based on one mole of tetrafluoroethylene or hexafluoropropylene.

At least one selected from the group consisting of initiator, UV and heat can be used as free radical generators. When a free radical generator is UV, UV from middle-pressure mercury lamp and high-pressure mercury lamp is exemplified. When a free radical generator is heat, 250–300° C. is exemplified. Initiators include peroxides, preferably peroxide having a half life of about 10 hours at a reaction temperature.

Preferable free radical generators are perbutyl D (di-t-butylperoxide), perbutyl O (t-butylperoxy-2-ethylhexanoate) and perbutyl I (t-butylperoxy-isopropylcarbonate). The preferable free radical generators are usually used in an amount of about 0.005–0.1 mole based on one mole of tetrafluoroethylene or hexafluoropropylene.

(1) With Regard to First Invention

As shown in FIG. 1, the reaction mixture comprising methanol and tetrafluoroethylene or hexafluoropropylene are fed from a reactor to a distillation column after completion of reaction. HF and water are included in the reaction mixture at about 300–1,000 ppm, respectively. The distillation column is heated to distill off methanol from the top of the column. Methanol is located at the upper part of the column, and fluoroalcohol is located at the lower part of the column. HF and water are located at the middle part of the distillation column and concentrated at about 3,000 ppm to about 3%. The layer in which HF and water are concentrated is removed from the distillation column as side cut. Temperature of side cut is about 80–120° C./0.1 MPa.

Figure 3:
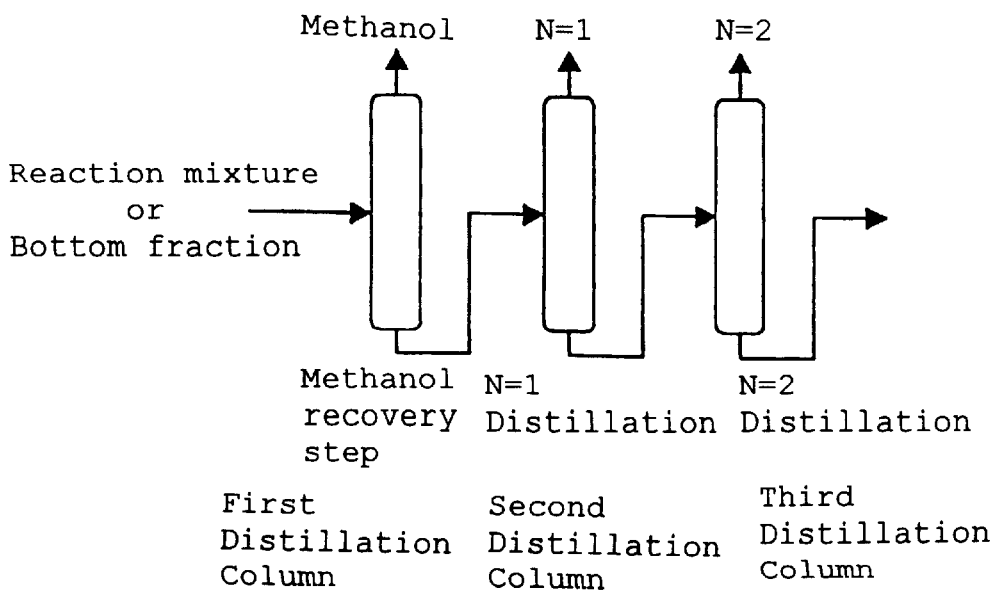
FIG. 3 shows a further embodiment of the invention.

The bottom fraction is subjected to a purification procedure to recover the fluoroalcohol represented by formula (1). Since a mixture comprising fluoroalcohols such as $HCF_2CF_2CH_2OH$ and $H(CF_2CF_2)_2CH_2OH$ is generated when tetrafluoroethylene is used for reaction, $HCF_2CF_2CH_2OH$ and $H(CF_2CF_2)_2CH_2OH$ may be separated sequentially in a purification procedure as shown in FIG. 3.

(2) With Regard to Second Invention

A reaction mixture comprising methanol and tetrafluoroethylene or hexafluoropropylene is fed into a first distillation column after completion of the reaction. The first distillation column is heated to distill off methanol from the top of the column. Components other than methanol are withdrawn from the bottom of the first distillation column and fed into a second distillation column. Methanol from the top of the first distillation column is recycled to a reactor. A fraction comprising HF and water is distilled off from the top of the second distillation column. A mixture comprising fluoroalcohols is withdrawn from the bottom of the second distillation column and subjected to a purification procedure to purify the desired fluoroalcohol represented by formula (1).

The fluoroalcohol of the invention is suitable for a solvent in the manufacture of an information recording medium comprising a substrate and as built thereon a recording layer adapted for laser writing and/or reading.

The information recording medium comprising a substrate and as built thereon a recording layer adapted for laser writing and/or reading can be manufactured by dissolving a dye in a solvent containing the fluoroalcohol of general formula (1) according to the invention, preferably a fluorine-containing solvent comprising said fluoroalcohol and, using the resulting dye solution, carrying out the routine series of operations inclusive of coating a substrate with it and drying the coated substrate to form a dye-containing recording layer. The dye mentioned above includes but is not limited to cyanine dyes, phthalocyanine dyes, pyrylium dyes, thiopyrylium dyes, squarylium dyes, azulenium dyes, indophenol dyes, indoaniline dyes, triphenylmethane dyes, quinone dyes, aminium dyes, diimmonium dyes, and metal complex dyes. The raw material for the substrate includes plastics such as polycarbonates, poly(methyl methacrylate), epoxy resin, amorphous polyolefins, polyesters and poly(vinyl chloride), glass and ceramics. For the purpose of improving surface smoothness and adhesion or preventing degradation of the recording layer, a primer coating or undercoating may be provided between the recording layer and the substrate, and also a protective layer may be formed on the recording layer.

In accordance with the invention, there can be easily provided substantially impurity-free $HCF_2CF_2CH_2OH$, $H(CF_2CF_2)_2CH_2OH$ and $HCF(CF_3)CF_2CH_2OH$ which are suited for use in the manufacture of an information recording medium comprising a substrate and as built thereon a recording layer adapted for laser writing and/or reading (optical disks such as CD-R and DVD-R) or photosensitive material for film.

BEST MODE FOR CARRYING OUT THE INVENTION

The invention is described below in detail by way of examples.

Example 1

Methanol (2L), di-t-butylperoxide (45 g) and calcium carbonate (30 g) were added to an autoclave. The air in the reactor was replaced by nitrogen. Tetrafluoroethylene was fed to the reactor at an initial rate of 600 g/hr, and the mixture was reacted for 6 hours by controlling a temperature at 125° C. and a pressure at 0.8 MPa.

According to the flow chart as shown in FIG. 1, the reaction mixture was separated into a top fraction containing methanol, a side cut containing HF and water, and a bottom fraction containing a fluoroalcohol. As shown in FIG. 3, $HCF_2CF_2CH_2OH$ and $H(CF_2CF_2)_2CH_2OH$ are separated sequentially from the bottom fraction.

Separation was conducted as follows.

The reaction mixture containing 300–1,000 ppm of HF and 300–1,000 ppm of water was fed into a distillation column. Still was heated with controlling a pressure of distillation column at 0.1 MPa.

Methanol was distilled off from the top of the distillation column at a distillation temperature of 80 to 90° C. Methanol from the top of the distillation column contains 10 ppm or less, preferably 5 ppm or less, more preferably 2 ppm or less of HF, and 3,000 ppm or less, preferably 1,000 ppm or less, more preferably 500 ppm or less of water.

A side cut which mainly contained methanol and $HCF_2CF_2CH_2OH$, and also HF and water each of which had a concentration ranging from 3,000 ppm to 3% was withdrawn from the middle part of the distillation column at a distillation temperature of 80–120° C.

A fluoroalcohol mixture was withdrawn from the bottom of the distillation column and subjected to a purification procedure by distillation to separate and purify $HCF_2CF_2CH_2OH$ and $H(CF_2CF_2)_2CH_2OH$ in this sequence.

Example 2

Figure 2:
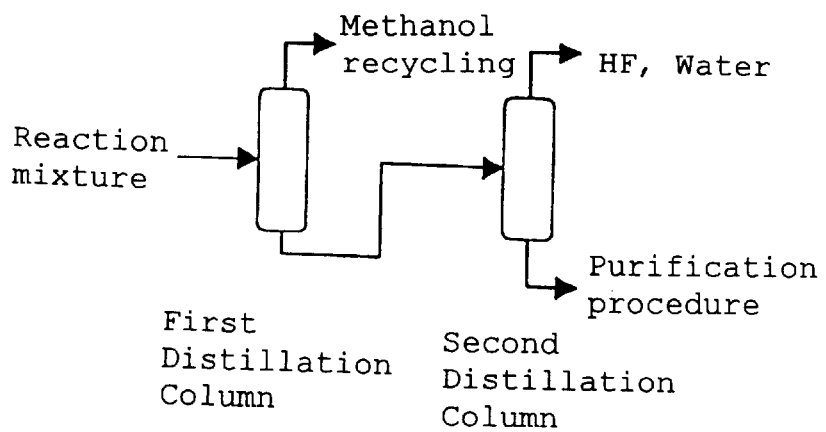
FIG. 2 shows another embodiment of the invention.

The reaction mixture obtained in example 1 was separated into a top fraction of first distillation column containing methanol, a top fraction of second distillation column containing HF and water, and a bottom fraction of the second distillation column containing fluoroalcohols according to the flow chart as shown in FIG. 2.

Separation was conducted as follows.

The reaction mixture containing 300–1,000 ppm of HF and 300–1,000 ppm of water was fed into a first distillation column. Still was heated with controlling a pressure of the first distillation column at 0.1 MPa.

Methanol was distilled off from the top of the first distillation column at distillation temperature of 80 to 90° C.

A mixture which mainly contained methanol and fluoroalcohol, and also HF and water was withdrawn from the bottom of the first distillation column and fed into a second distillation column.

Still was heated with controlling a pressure of the second distillation column at 0.1 MPa.

A fraction which contained methanol, HF and water was distilled off from the top of the second distillation column at a distillation temperature of 80–120° C.

A fluoroalcohol mixture was withdrawn from the bottom of the second distillation column and subjected to a purification procedure by distillation to separate and purify $HCF_2CF_2CH_2OH$ and $H(CF_2CF_2)_2CH_2OH$ in this sequence.

In addition, as shown in FIG. 3, $HCF_2CF_2CH_2OH$ and $H(CF_2CF_2)_2CH_2OH$ may be separated simultaneously by the steps of: recovering methanol from a first distillation column into which a reaction mixture or a bottom fraction prepared by removing methanol is fed; distilling a bottom fraction from the first distillation column in a second distillation column to separate $HCF_2CF_2CH_2OH$ (N=1); and distilling a bottom fraction from the second distillation column in a third distillation column to separate $H(CF_2CF_2)_2CH_2OH$ (N=2).

What is claimed is:

1. A method for manufacturing a fluoroalcohol represented by formula (1)

$$H(CFR^1CF_2)_nCH_2OH \qquad (1)$$

(wherein $R^1$ represents F or $CF_3$, when n=1; $R^1$ represents F, when n=2) by reacting methanol with tetrafluoroethylene or hexafluoropropylene in the presence of a free radical generator, wherein the method comprises the steps of:

feeding a reaction mixture into a distillation column; distilling off methanol from the top of the distillation column;

withdrawing a bottom fraction comprising the fluoroalcohols from the bottom of the distillation column;

removing a side cut comprising water and HF from the distillation column;

feeding methanol from the top of the distillation column back into a reactor for recycling; and purifying the bottom fraction to recover the fluoroalcohol represented by formula (1).

2. A method for manufacturing a fluoroalcohol represented by formula (1)

$$H(CFR^1CF_2)_nCH_2OH \qquad (1)$$

(wherein $R^1$ represents F or $CF_3$, when n=1; $R^1$ represents F, when n=2) by reacting methanol with tetrafluoroethylene or hexafluoropropylene in the presence of a free radical generator, wherein the method comprises the steps of:

feeding a reaction mixture into a first distillation column;

distilling off methanol from the top of the first distillation column;

withdrawing a first bottom fraction comprising water, HF and the fluoroalcohol represented by formula (1) from the bottom of the first distillation column;

feeding the first bottom fraction into a second distillation column;

withdrawing a fraction comprising water and HF from the top of the second distillation column;

withdrawing a second bottom fraction comprising the fluoroalcohols represented by formula (1) from the bottom of the second distillation column;

feeding methanol from the top of the first distillation column back into a reactor for recycling; and purifying the second bottom fraction to recover the fluoroalcohol represented by formula (1).

* * * * *